US009974829B2

(12) United States Patent
Robinson et al.

(10) Patent No.: US 9,974,829 B2
(45) Date of Patent: *May 22, 2018

(54) METHODS AND USES OF SLIT FOR TREATING FIBROSIS

(71) Applicant: The Hospital for Sick Children, Toronto (CA)

(72) Inventors: Lisa Annette Robinson, Toronto (CA); Darren Arthur Vee-Yip Yuen, North York (CA)

(73) Assignee: The Hospital for Sick Children, Toronto (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/625,399

(22) Filed: Jun. 16, 2017

(65) Prior Publication Data

US 2017/0281726 A1    Oct. 5, 2017

Related U.S. Application Data

(63) Continuation of application No. 14/896,168, filed as application No. PCT/CA2014/000474 on Jun. 4, 2014, now Pat. No. 9,700,593.

(60) Provisional application No. 61/831,064, filed on Jun. 4, 2013.

(51) Int. Cl.
*A61K 38/00* (2006.01)
*A61K 38/17* (2006.01)
*A61K 45/06* (2006.01)

(52) U.S. Cl.
CPC .......... *A61K 38/1709* (2013.01); *A61K 45/06* (2013.01)

(58) Field of Classification Search
CPC ............................ A61K 38/1709; A61K 45/06
See application file for complete search history.

(56) References Cited

U.S. PATENT DOCUMENTS

| | | | |
|---|---|---|---|
| 8,399,404 B2 | 3/2013 | Robinson | |
| 8,680,044 B2 | 3/2014 | Robinson | |
| 9,572,879 B2 * | 2/2017 | Lu | C07K 14/70503 |
| 9,700,593 B2 * | 7/2017 | Robinson | A61K 38/1709 |
| 2011/0305732 A1 * | 12/2011 | Robinson | A61K 31/7105 424/400 |

FOREIGN PATENT DOCUMENTS

| | | |
|---|---|---|
| WO | 00/55321 A3 | 9/2000 |
| WO | 2010/068917 A2 | 6/2010 |

OTHER PUBLICATIONS

Kanellis, J. et al., "Modulation of Inflammation by Slit Protein in Vivo in Experimental Crescentic Glomerulonephritis", American Journal of Pathology, Jul. 2004, vol. 165, No. 1, pp. 341-352.
Chawla, L.S. and Kimmel, P., "Acute kidney injury and chronic kidney disease: an integrated clinical syndrome", Kidney International, Jun. 2012, vol. 82, pp. 516-524.
Galkina, E. and Ley, K., "Leukocyte Recruitment and Vascular Injury in Diabetic Nephropathy", Journal of the American Society of Nephrology, 2006, vol. 17, pp. 368-377.
Friedman, S.L. et al., "Therapy for Fibrotic Diseases: Nearing the Starting Line", Science Translation Medicine, Jan. 9, 2013, vol. 5, No. 167, pp. 1-17.
Levey, A.S. et al., "National Kidney Foundation Practice Guidelines for Chronic Kidney Disease: Evaluation, Classification, and Stratification", Annals of Internal Medicine, Jul. 15, 2003, vol. 139, No. 2, pp. 137-e149.
Chaturvedi, S. and Robinson, L.A., "Slit2-Robo signaling in inflammation and kidney injury", Pediatric Nephrology, Apr. 29, 2014, pp. 1-6.
Yuen, D.A. and Robinson, L.A., "Slit2-Robo signaling: a novel regulator of vascular injury", Current Opinion in Nephrology, Jul. 2013, vol. 22. No. 4, pp. 445-451.
Chaturvedi, S. et al. "Slit2 Prevents Neutrophil Recruitment and Renal Ischemia-Reperfusion Injury", Journal of the American Society of Nephrology, 2013, vol. 24, pp. 1274-1287.
Morlot, C. et al., "Structural insights into the Slit-Robo complex", PNAS, Sep. 18, 2007, vol. 104, No. 38, pp. 14923-14928.
Sidiqi, A.M. et al., "Slit2-Robo Signaling as a Potential Target for Attenuating Early Diabetic Renal Hyperfiltration", poster, presented at Canadian Society of Nephrology Meeting, Vancouver, Canada, Apr. 2014.
Sidiqi, A.M. et al., "Robo Receptor Ratio Regulates Angiogenesis in the Diabetic Kidney", poster, presented at Canadian Society of Nephrology Meeting, Montreal, Canada, Apr. 2015.
Yuen, D.A. et al., "Recombinant N-Terminal Slit2 Inhibits TGF-β-Induced Fibroblast Activation and Renal Fibrosis", JASN, published ahead of print Feb. 11, 2016, vol. 27, pp. 1-7.

* cited by examiner

*Primary Examiner* — Marcela M Cordero Garcia
(74) *Attorney, Agent, or Firm* — Bereskin & Parr LLP; Melanie Szweras

(57) ABSTRACT

The present disclosure provides methods and uses of Slit protein and nucleic acid for inhibiting fibrosis and fibrotic-related disorders, for example, of the kidney, lung, heart, liver, or a wound. The Slit protein can be, for example, Slit2 or Slit2-N, or a Slit variant that can bind the Robo receptor and induce signalling. Also provided are pharmaceutical compositions comprising the Slit protein or nucleic acid and an additional anti-fibrotic agent.

17 Claims, 9 Drawing Sheets

METHODS AND USES OF SLIT FOR TREATING FIBROSIS

RELATED APPLICATION

This application is a continuation of U.S. patent application Ser. No. 14/896,168 filed Dec. 4, 2015 (now allowed), which is a national phase entry of PCT/CA2014/000474 filed Jun. 4, 2014 (which designates the U.S.) which claims priority from U.S. Provisional application No. 61/831,064 filed Jun. 4, 2013, the contents of both of which are incorporated herein by reference in their entirety.

FIELD

The present disclosure relates to methods and uses for inhibiting fibrosis and for treating associated conditions and diseases comprising administering a Slit protein or nucleic acid. The disclosure also relates to pharmaceutical compositions comprising Slit protein or a nucleic acid thereof and an anti-fibrotic agent.

BACKGROUND

Conventional wisdom predicted that the majority of previously healthy patients who developed acute kidney injury (AKI) would recover without significant renal sequelae. However, recent large studies indicate that even healthy patients are at significant risk of developing chronic kidney disease (CKD) and end-stage renal disease (ESRD) after one episode of AKI (Chawla et al., 2011; Lo et al., 2009; Amdur et al., 2009; Wald et al., 2009; Chawla and Kimmel, 2012). An Ontario study examined over 41,000 patients who survived an episode of AKI without requiring acute dialysis at the time of the AKI (Wald et al., 2012). Compared to matched control patients, the patients with AKI had a near 3-fold increase in late ESRD necessitating chronic dialysis (Wald et al., 2012). Thus, even a single episode of what would previously have been regarded as "mild" AKI sets the stage for later CKD and ESRD.

Ischemia-reperfusion-injury (IRI) is a cause of AKI and may progress to CKD (also known as chronic renal injury) as a result of progressive renal fibrosis, in which normal elements of the renal tubulointerstitium are replaced by myofibroblasts that secrete collagenous extracellular matrix (Bonventre and Yang, 2011; Quaggin and Kapus, 2011; Venkatachalam et al., 2010). The main features include recruitment and proliferation of myofibroblasts which secrete collagenous extracellular matrix, and loss of capillary density (Zeisberg and Neilson, 2010). Eventually, the normal tubular and vascular structures of the renal interstitium undergo atrophy and become replaced by fibrous scar. Once recruited to the tubulointerstitium, pericytes become myofibroblasts. In response to locally produced fibrogenic cytokines and growth factors, especially transforming growth factor beta (TGF-β), myofibroblasts proliferate and secrete abundant quantities of extracellular matrix proteins, particularly collagen type I and fibronectin (Kida and Duffield, 2011; Schrimpf and Duffield, 2011; Lin et al., 2011). The net result is replacement of functional nephrons by scar tissue and progressive kidney failure.

Diabetes is the leading cause of chronic kidney disease in most countries around the world [Rossing 2006]. In the United States alone, it is estimated that nearly $17 billion is spent annually on diabetic nephropathy care [Gordois et al. 2004]. While glycemic control [Diabetes Control and Complications Trial Research Group 1993, UKPDS 1998], blood pressure regulation [Adler et al. 2000], and renin-angiotensin system blockade [Lewis et al. 2001; Brenner et al. 2001; Lewis et al. 1993] slow nephropathy progression, many patients still progress to kidney failure, a costly and life-threatening condition requiring renal replacement therapy. New treatments are clearly needed.

Diabetic nephropathy is driven by a complex set of inter-related pathways. Early on, diabetes is commonly characterized by hyperfiltration, a phenomenon that has been linked epidemiologically [Costacou et al. 2009, Magee et al. 2009; Ruggenenti et al. 2012] and mechanistically [Anderson et al. 1986] to poor long-term renal outcomes. While classically felt to be driven by altered renal hemodynamics [Anderson et al. 1993, Sochet et al. 2006], emerging evidence suggests that glomerular angiogenesis also augments GFR through increases in filtration surface area created by nascent capillaries [Osterby et al. 1988, Hirose et al. 1980]. Later, diabetic nephropathy is characterized by fibrosis, a largely irreversible process that obliterates both glomeruli and the tubulointerstitium [Gilbert et al. 1999]. Transforming growth factor-β (TGF-β) is a central driver of diabetic fibrogenesis, activating a variety of pro-fibrotic signaling pathways. In particular, two TGF-β signaling intermediates, the Receptor Smads (Smad2 and Smad3) and RhoA, mediate fibrogenesis via both independent and inter-related mechanisms [Engel et al. 1999; Bhowmick et al. 2001]. While anti-TGF-β therapies may block fibrosis, they also inhibit other critical non-fibrogenic TGF-β effects, including its potent immunosuppressive activity. Thus, anti-TGF-β blockade has been a largely unsuccessful treatment strategy for diabetic nephropathy.

The Slit family of proteins, together with their transmembrane receptor, Roundabout (Robo), were initially shown to repel axons and neuronal migration during development of the central nervous system (CNS) (Brose et al., 1999; Kidd et al., 1999). There are three known mammalian Slit family members. Slit1 is predominantly expressed in the CNS, while Slit2 and, to a lesser degree, Slit3 are expressed in other tissues, especially kidney, heart, and lung (Wu et al., 2001). Slit protein expression persists into adulthood, suggesting roles beyond those during development. Slit proteins are structurally unique, having both epidermal-like growth factor and leucine-rich repeats (LRR). These features allow secreted Slit to interact with varied proteins, including cell surface receptors and extracellular matrix proteins such as glypican-1 (Ronca et al., 2001). Thus, Slit can act as a local, non-diffusible signaling molecule. Proteolytic cleavage of Slit2, perhaps by metalloproteases, generates N- and C-terminal fragments (Slit-N and Slit-C) (Brose et al., 1999; Schimmelpfeng et al., 2001; Wang et al., 1999). Slit2-N is sufficient to engage its receptor and to induce signaling (Nguyen et al., 2001; Battye et al., 2001; Chen et al., 2001).

Robo is a single-pass type 1 transmembrane protein. The extracellular region contains five immunoglobulin (Ig)-like domains and three fibronectin type III repeats while the intracellular domain contains four conserved cytoplasmic motifs (CC0, CC1, CC2, and CC3). The extracellular Ig-like domains of Robo are sufficient for binding the LRR of Slit. The intracellular CC3 motif is necessary for the repulsive response to Slit. Mammals have four Robo isoforms, of which Robo-1 is most widely expressed in non-neural cells, especially immune cells (Wu et al., 2001; Prasad et al., 2007; Tole et al., 2009).

After Slit2 binds to the extracellular domain of Robo-1, the intracellular domain of Robo-1 associates with a novel family of GTPase activating proteins (GAPs), namely Slit-Robo GAPs (srGAP) (Wong et al., 2001). By preventing activation of Cdc42, Slit2 inhibited migration of cells from the anterior subventricular zone of the forebrain ((Wong et al., 2001). Recent studies examined the effects of Slit2 on migration of vascular smooth muscle cells (VSMC), lymphocytes, and neutrophils towards platelet-derived growth factor B (PDGF), the chemokine CXCL12, and formyl-methionyl-leucyl-phenylalanine (fMLP), respectively (Prasad et al., 2007; Tole et al., 2009; Liu et al., 2006). These chemoattractants induce cell migration by activating Rac, Cdc42, and/or Rho, crucial for reorganization of the cytoskeleton. Slit2 inhibited activation of Rac, Cdc42 and/or Rho, and consequent migration of VSMC, lymphocytes, and neutrophils (Prasad et al., 2007; Tole et al., 2009; Liu et al., 2006). The present inventors and others also showed that Slit2 inhibits migration of leukocytes and cancer cells, and inhibits platelet adhesion by preventing activation of Akt and Erk MAPK (Patel et al., 2012; Prasad et al., 2007; Tole et al., 2009; Prasad et al., 2004).

During kidney development Slit and Robo signaling restrict inappropriate migration of cells (Piper et al., 2000; Grieshammer et al., 2004; Yu et al., 2004). In fact, mutant mice lacking Slit2 do not develop a single ureteric bud, but rather, supernumerary ureteric buds that remain abnormally connected to the nephric duct (Grieshammer et al., 2004).

In adult rodent and human kidneys, Slit2 is expressed by many cell types, including vascular endothelial cells, glomerular endothelial, mesangial and epithelial cells, and tubular epithelial cells (Wu et al., 2001; Kanellis et al., 2004). In an animal model of crescentic glomerulonephritis, endogenous glomerular expression of Slit2 sharply decreased, promoting enhanced inflammation (Kanellis et al., 2004). When Slit2 was administered systemically in this short-term inflammatory model, renal function and renal histology improved significantly (Kanellis et al., 2004).

In U.S. Pat. No. 8,399,404, it was shown that, in a mouse model of IRI in which both renal pedicles are clamped, Slit2 and Slit2-N were shown to prevent renal failure due to acute kidney injury.

Chronic fibrosis after acute or repeated injury is not unique to the kidney, and results in conditions such as chronic obstructive lung disease, cardiomyopathy and heart failure, and liver cirrhosis. In all of these disorders, fibroblast activation occurs and the normal tissue becomes irreversibly replaced by fibrotic scar tissue.

SUMMARY

The present inventors have shown that Roundabout (Robo) receptors are expressed on fibroblasts and have further shown that Slit2, which binds the Robo receptor, improves kidney function and inhibits collagen deposition and fibrosis in models of chronic kidney disease.

Accordingly, in one aspect, the present disclosure provides a method of inhibiting fibrosis comprising administering a Slit protein or nucleic acid to a cell or animal in need thereof. Also provided is use of a Slit protein or nucleic acid for inhibiting fibrosis in a cell or animal in need thereof. Further provided is use of a Slit protein or nucleic acid in the manufacture of a medicament for inhibiting fibrosis in a cell or animal in need thereof. Also provided is a Slit protein or nucleic acid for use in inhibiting fibrosis in a cell or animal in need thereof.

In one embodiment, the fibrosis is due to the accumulation of extracellular matrix, such as collagen or fibrinogen.

In one embodiment, the fibrosis is kidney fibrosis, lung fibrosis, cardiac fibrosis, liver fibrosis or excessive fibrosis deposited due to a wound. In a particular embodiment, the fibrosis is kidney fibrosis.

In another aspect, the present disclosure provides a method of treating a fibrotic-related disorder, condition or disease comprising administering a Slit protein or nucleic acid to a cell or animal in need thereof. Also provided is use of a Slit protein or nucleic acid for treating a fibrotic-related disorder, condition or disease in a cell or animal in need thereof. Further provided is use of a Slit protein or nucleic acid in the manufacture of a medicament for treating a fibrotic-related disorder, condition or disease in a cell or animal in need thereof. Even further provided is a Slit protein or nucleic acid for use in treating a fibrotic-related disorder, condition or disease in a cell or animal in need thereof.

In an embodiment, the fibrotic-related disorder, condition or disease is glomerulonephritis, diabetic nephropathy, lupus nephritis, toxic nephropathy, chronic pyelonephritis, polycystic kidney disease, renal scarring, wound scarring, post-cardiac infarction, cystic fibrosis, idiopathic pulmonary fibrosis, cirrhosis, chronic obstructive pulmonary disease, cardiomyopathy, or all other progressive diseases marked by fibrosis. In a particular embodiment, the fibrotic-related disorder is diabetic nephropathy.

In some embodiments of the methods and uses disclosed herein, the Slit protein or nucleic acid is administered or used locally. In some embodiments, the Slit protein or nucleic acid is administered or used chronically or long-term. In some embodiments, the Slit protein or nucleic acid is administered or used daily, weekly or monthly.

In another aspect, the present disclosure provides a method of treating chronic kidney disease comprising administering a Slit protein or nucleic acid to a cell or animal in need thereof. Also provided is use of a Slit protein or nucleic acid for treating chronic kidney disease in a cell or animal in need thereof. Further provided is use of a Slit protein or nucleic acid in the manufacture of a medicament for treating chronic kidney disease in a cell or animal in need thereof. Even further provided is a Slit protein or nucleic acid for use in treating chronic kidney disease in a cell or animal in need thereof.

In one embodiment, the Slit protein or nucleic acid is administered 5 days after acute kidney injury, or later. In another embodiment, the Slit protein or nucleic acid is administered 10 days after acute kidney injury, or later. In yet another embodiment, the Slit protein or nucleic acid is administered or used 14 days, 1 month, or 6 months after acute kidney injury, or later.

In an embodiment, the subject with chronic kidney disease has a glomerular filtration rate of less than 60 ml/min/1.73 m$^2$. In another embodiment, the subject with chronic kidney disease is at stage 3 or greater CKD.

In yet another aspect, the present disclosure provides a method of prophylactically treating a subject at risk of fibrosis comprising administering a Slit protein or nucleic acid to the cell or animal in need thereof. Also provided is use of a Slit protein or nucleic acid for prophylactically treating subject at risk of fibrosis in a cell or animal in need thereof. Further provided is use of a Slit protein or nucleic acid in the manufacture of a medicament for prophylactically treating subject at risk of fibrosis in a cell or animal in need thereof. Even further provided is a Slit protein or nucleic acid for use in prophylactically treating subject at risk of fibrosis in a cell or animal in need thereof.

In an embodiment, the Slit protein is Slit1, 2 or 3, or a variant thereof that binds the Robo receptor and induces signaling. In one embodiment, the Slit protein is Slit2 or Slit2-N.

In a further aspect, the present disclosure provides a pharmaceutical composition comprising a Slit protein or nucleic acid and an additional anti-fibrotic agent. In one embodiment, the Slit protein is Slit1, 2 or 3, or a variant thereof that binds the Robo receptor and induces signaling. In another embodiment, the Slit protein is Slit2 or Slit2-N.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

glomerular endothelial volume. *p<0.05 vs. control. † p<0.05 vs. vehicle-treated diabetic rats.

Figure 8:
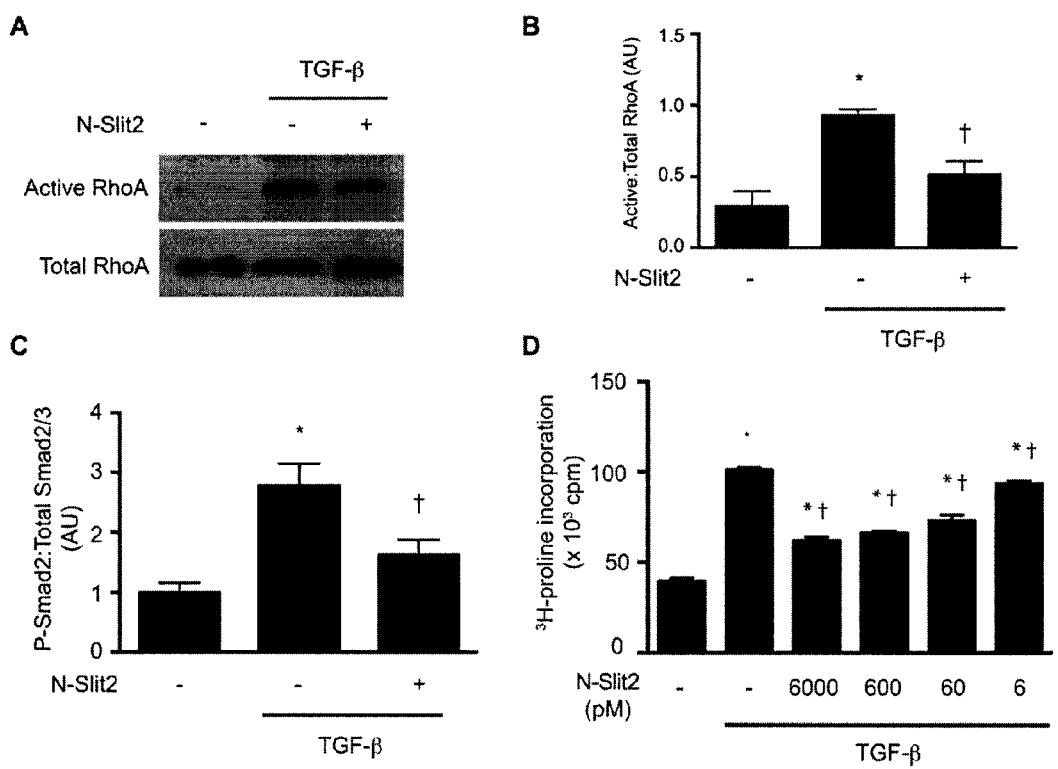

FIG. 8 shows A bioactive N-terminal Slit2 fragment (N-Slit2) inhibits TGF-β-induced (A-B) RhoA activation and (C) Smad2 phosphorylation, two key pro-fibrotic signaling pathways activated by TGF-β. (D) N-Slit2 treatment also inhibited TGF-β-induced collagen production (as measured by a $^3$H-proline incorporation assay). N-Slit2 treatment concentration was 30 nM unless otherwise specified. *p<0.05 vs. control. † p<0.05 vs. TGF-β stimulation.

Figure 9:
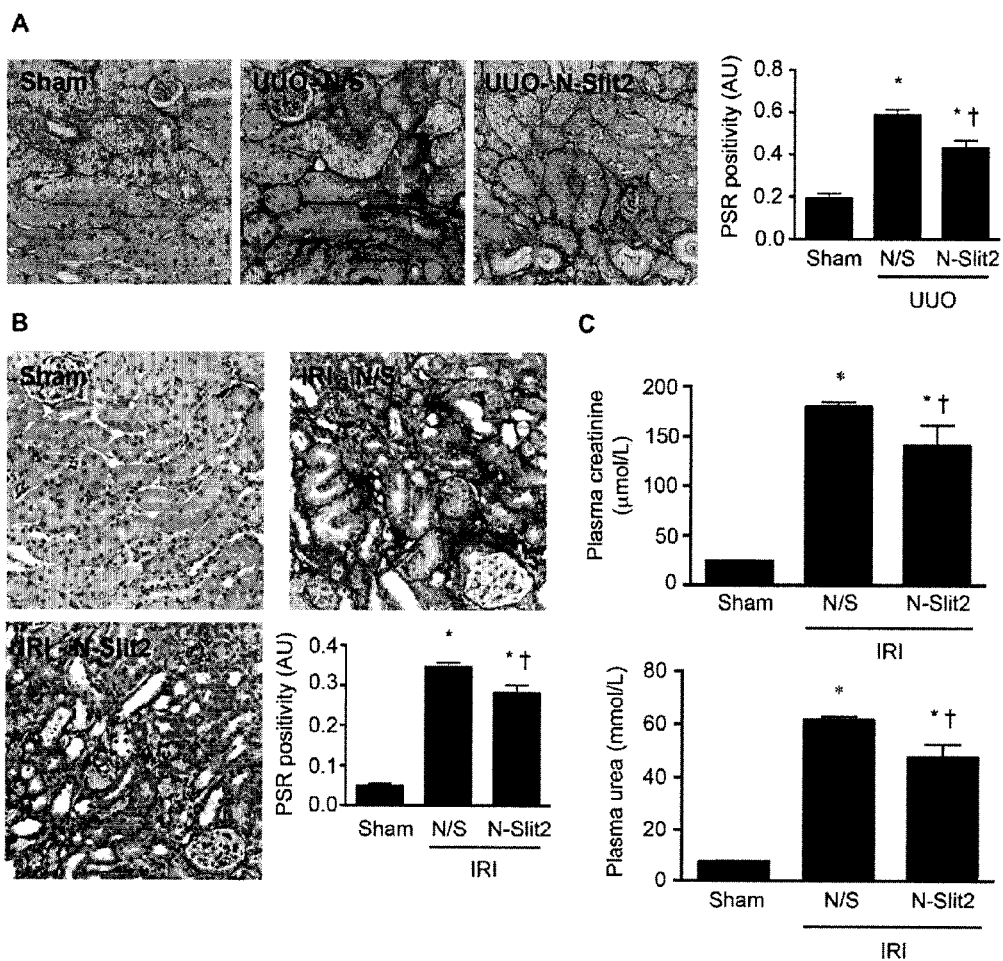

FIG. 9 shows (A) Male C57BL/6 mice underwent unilateral left ureteral obstruction or sham surgery. UUO mice were randomized to receive either 2 μg N-Slit2 (n=12), or normal saline (N/S) vehicle control (n=11). N-Slit2 and N/S were administered via intravenous injection 1 h prior to IRI, followed by an intra-peritoneal injection 3 days following the surgery. Animals were followed for a total of 7 days, sacrificed, and the left kidneys stained with picrosirius red (PSR) to identify fibrillar collagen with red staining. Whole-section digital analysis of PSR-stained kidneys demonstrated a significant increase in fibrillar collagen deposition in normal saline (N/S)-treated UUO mice compared with sham mice. N-Slit2 treatment partially attenuated this fibrotic response. Representative 20× images and quantitative analysis. *p<0.05 vs. sham controls. † p<0.05 vs. N/S vehicle-treated UUO mice. Abbreviations: AU, arbitrary units. (B) Male C57BL/6 mice underwent unilateral left kidney ischemia-reperfusion injury, characterized by renovascular pedicle clamping for 45 min under anesthesia, followed by clamp release and reperfusion. IRI mice were randomized to receive either 2 μg N-Slit2 (n=8), or normal saline (N/S) vehicle control (n=11). N-Slit2 and N/S were administered via intravenous injection 1 h prior to IRI, followed by thrice weekly intra-peritoneal injections in the 2 weeks following the surgery. A subset of mice underwent sham surgery during which kidneys were mobilized but uninjured to serve as healthy controls. Animals were followed for a total of 14 days, and then sacrificed for tissue and molecular analysis. Fourteen days after surgery, sham and IRI mice were sacrificed, and the left kidneys stained with picrosirius red (PSR) to identify fibrillar collagen with red staining. Whole-section digital analysis of PSR-stained kidneys demonstrated a significant increase in fibrillar collagen deposition in normal saline (N/S)-treated IRI mice compared with sham mice. N-Slit2 treatment partially attenuated this fibrotic response. Representative 20× images and quantitative analysis. *p<0.05 vs. sham controls. † p<0.05 vs. N/S vehicle-treated IRI mice. Abbreviations: AU, arbitrary units. (C-D) One day prior to sacrifice (ie 13 days after surgery), all animals from the experiment described in panel (B) underwent nephrectomy to remove the healthy right kidney. Blood was then collected prior to sacrifice, centrifuged, and plasma collected for measurement of renal function. (C) Plasma creatinine. (D) Plasma urea. *p <0.05 vs. sham operated controls. † p<0.05 vs. normal saline vehicle-treated IRI animal.

DETAILED DESCRIPTION

The present inventors have demonstrated that Slit2, which was previously known to inhibit platelet coagulation and acute kidney injury, also inhibits fibrosis and improves renal function in a model of chronic kidney disease. The present inventors have further shown that the Robo-1 receptor, to which Slit proteins bind, is expressed by fibroblasts.

Accordingly, in one aspect, the present disclosure provides a method of inhibiting fibrosis comprising administering a Slit protein or nucleic acid to a cell or animal in need thereof. Also provided is use of a Slit protein or nucleic acid for inhibiting fibrosis in a cell or animal in need thereof. Further provided is use of a Slit protein or nucleic acid in the manufacture of a medicament for inhibiting fibrosis in a cell or animal in need thereof. Also provided is a Slit protein or nucleic acid for use in inhibiting fibrosis in a cell or animal in need thereof.

The phrase "inhibiting fibrosis" as used herein refers to preventing or reducing extracellular matrix fibers from accumulating in tissue.

The term "extracellular matrix" as used herein refers to fibers that are typically secreted from a cell that reside in the extracellular space and include without limitation, collagen and fibronectin.

Inhibiting fibrosis as used herein refers to a decrease of at least 5%, 10%, 20%, 30%, 40%, 50%, 60%, 70%, 80% or more of extracellular matrix accumulation compared to an untreated control or reference value. In one embodiment, the extracellular matrix accumulation is characterized by collagen deposition and/or increased collagen synthesis and inhibition of extracellular matrix accumulation is due to a decrease in collagen deposition and/or synthesis.

In some embodiments, inhibiting fibrosis is useful in treating a variety of diseases and conditions, including without limitation, kidney fibrosis, lung fibrosis, cardiac fibrosis, liver fibrosis, or excessive fibrosis deposited due to a wound. In a particular embodiment, the fibrosis is kidney fibrosis.

Accordingly, the present disclosure provides a method of treating a fibrotic-related disorder, condition or disease comprising administering a Slit protein or nucleic acid to a cell or animal in need thereof. Also provided is use of a Slit protein or nucleic acid for treating a fibrotic-related disorder, condition or disease in a cell or animal in need thereof. Further provided is use of a Slit protein or nucleic acid in the manufacture of a medicament for treating a fibrotic-related disorder, condition or disease in a cell or animal in need thereof. Also provided is a Slit protein or nucleic acid for use in treating a fibrotic-related disorder, condition or disease in a cell or animal in need thereof.

The term "fibrotic disorder, condition or disease" as used herein refers to a disorder, condition or disease that results in increased fibrosis and scarring, typically, over an extended period of time, and includes without limitation, glomerulonephritis, diabetic nephropathy, lupus nephritis, toxic nephropathy, chronic pyelonephritis, polycystic kidney disease, renal scarring, wound scarring, post-cardiac infarction, cystic fibrosis, idiopathic pulmonary fibrosis, cirrhosis, chronic obstructive pulmonary disease, cardiomyopathy, and all other progressive diseases marked by fibrosis. In a particular embodiment, the fibrotic disorder, condition or disease is diabetic nephropathy.

In some embodiments of the methods and uses disclosed herein, the Slit protein or nucleic acid is administered or used locally. In some embodiments, the Slit protein or nucleic acid is administered or used chronically or long-term, for a period ranging from weeks to years. In some embodiments, the Slit protein or nucleic acid is administered daily, weekly or monthly.

In one embodiment, the present disclosure provides a method of treating chronic kidney disease comprising administering a Slit protein or nucleic acid to a cell or animal in need thereof. Also provided is use of a Slit protein or nucleic acid for treating chronic kidney disease in a cell or animal in need thereof. Further provided is use of a Slit protein or nucleic acid in the manufacture of a medicament for treating chronic kidney disease in a cell or animal in need thereof. Also provided is a Slit protein or nucleic acid for use in treating chronic kidney disease in a cell or animal in need thereof.

The term "chronic kidney disease" as used herein refers to the progressive loss of kidney function over a period of months or years. In one embodiment, the kidney disease follows from an acute kidney injury.

In an embodiment, the subject with chronic kidney disease has a glomerular filtration rate of less than 60 ml/min/ 1.73 m$^2$. In another embodiment, the subject with chronic kidney disease is at stage 3 or greater CKD.

A person skilled in the art would understand that chronic kidney disease refers to a chronic progressive loss of function over weeks, months or years after an initial injury or onset of disorder. In contrast, acute kidney injury is short-term and is marked by influx of neutrophils, T lymphocytes, and monocytes/macrophages into the kidney within the first 48 hours post-injury.

Accordingly, in one embodiment, the Slit protein or nucleic acid is administered 5 days after acute kidney injury, or later. In another embodiment, the Slit protein or nucleic acid is administered 10 days after acute kidney injury, or later. In yet another embodiment, the Slit protein or nucleic acid is administered or used 14 days, 1 month, or 6 months after acute kidney injury, or later.

In other embodiments, the present disclosure provides methods and uses for inhibiting fibrosis comprising prophylactically treating a subject at risk for fibrosis, including without limitation, subjects with post-acute kidney injury, diabetes, chronic glomerulonephritis, lupus nephritis, toxic nephropathy, chronic pyelonephritis, polycystic kidney disease, renal scarring, wound scarring, post-cardiac infarction, cystic fibrosis, idiopathic pulmonary fibrosis, cirrhosis, chronic obstructive pulmonary disease, cardiomyopathy, and all other progressive diseases marked by fibrosis.

Accordingly, the present disclosure also provides a method of prophylactically treating a subject at risk of fibrosis comprising administering a Slit protein or nucleic acid encoding a Slit protein to a cell or animal in need thereof. Also provided is use of a Slit protein or nucleic acid for prophylactically treating a subject at risk of fibrosis in a cell or animal in need thereof. Further provided is use of a Slit protein or nucleic acid in the manufacture of a medicament for prophylactically treating a subject at risk of fibrosis in a cell or animal in need thereof. Also provided is a Slit protein or nucleic acid for use in prophylactically treating a subject at risk of fibrosis in a cell or animal in need thereof.

In one embodiment, the present disclosure provides a method of prophylactically treating a subject at risk of fibrosis comprising instilling a Slit protein or nucleic acid encoding a Slit protein locally, via an indwelling catheter, or systemically. Also provided is use of a Slit protein or nucleic acid encoding a Slit protein for instillation locally, via an indwelling catheter, or systemically, to treat a subject at risk of fibrosis. Further provided is use of a Slit protein or nucleic acid encoding a Slit protein in the preparation of a medicament for instillation locally, via an indwelling catheter, or systemically, in a subject at risk of fibrosis. Also provided is a Slit protein or nucleic acid encoding a Slit protein for use in instillation locally, via an indwelling catheter, or systemically, in a subject at risk of fibrosis.

The phrase "prophylactically treating a subject at risk of fibrosis" refers to treating a subject that has had an injury that typically results in scarring or fibrosis prior to any evidence of scarring or fibrosis. In an embodiment, the subject is prophylactically treated chronically, for example, for more than 5 days, more than 10 days, more than two weeks, more than 1 month after initial injury.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

The term "a cell" as used herein includes a plurality of cells and refers to all types of cells. Administering a compound to a cell includes in vivo, ex vivo and in vitro treatment.

The term "animal" or "subject" as used herein includes all members of the animal kingdom, optionally mammal. The term "mammal" as used herein is meant to encompass, without limitation, humans, domestic animals such as dogs, cats, horses, cattle, swine, sheep, goats, and the like, as well as wild animals. In an embodiment, the mammal is human.

The term "effective amount" as used herein means a quantity sufficient to, when administered to an animal, effect beneficial or desired results, including clinical results, and as such, an "effective amount" depends upon the context in which it is being applied. For example, in the context of inhibiting platelet coagulation, it is the amount of the a Slit protein or nucleic acid sufficient to achieve such an inhibition as compared to the response obtained without administration of the a Slit protein or nucleic acid.

The term "Slit protein" as used herein is intended to refer to any one of a family of proteins known to be ligands for the Roundabout receptor (Robo), including Slit1, Slit2 and Slit3. The term "Slit" is intended to encompass the protein from any species or source, optionally, human Slit proteins. The term "Slit nucleic acid" is intended to encompass a nucleic acid encoding a Slit protein. The nucleic acid and protein sequences of human Slit1 are set forth as NM_003061 and NP_003052, respectively. The nucleic acid and protein sequences of human Slit2 are set forth as AF133270.1 and AAD25539, respectively. The nucleic acid and protein sequences of human Slit3 are set forth as NM_003062.2 and NP_003053.1, respectively. Slit sequences as set forth are incorporated by reference in their entirety.

In an embodiment, the Slit protein is Slit1, 2 or 3 or a variant thereof. In another embodiment, the Slit protein is Slit2 or Slit2-N or a variant thereof.

The term "Slit2-N" or "N-Slit2" as used herein refers to a truncated Slit2 protein comprising the N-terminal which contains the leucine rich region necessary for binding to the Robo-1 receptor and for downstream signal transduction.

The term "nucleic acid molecule" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "variant" as used herein includes modifications, substitutions, additions, derivatives, analogs, fragments or chemical equivalents of the Slit nucleic acid or amino acid sequences disclosed herein that perform substantially the same function in substantially the same way. For instance, the variants of the Slit peptides would have the same function, for example, of binding the Robo receptor, inducing signaling or inhibiting fibrosis.

Variants also include peptides with amino acid sequences that are substantially or essentially identical to the amino acid sequences of the Slit protein or nucleic acid molecules with nucleic acid sequence that are substantially or essentially identical to the nucleic acid sequence encoding the Slit proteins.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "sequence identity" as used herein refers to the percentage of sequence identity between two polypeptide and/or nucleotide sequences.

To determine the percent identity of two amino acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues at corresponding amino acid positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In other embodiments, to determine the percentage of identity between two polypeptide sequences, the amino acid sequences of such two sequences are aligned, for example using the Clustal W algorithm (Thompson, J D, Higgins D G, Gibson T J, 1994, Nucleic Acids Res. 22(22):4673-4680.), together with BLOSUM 62 scoring matrix (Henikoff S. and Henikoff J. G., 1992, *Proc. Natl. Acad. Sci.* USA 89: 10915-10919.) and a gap opening penalty of 10 and gap extension penalty of 0.1, so that the highest order match is obtained between two sequences wherein at least 50% of the total length of one of the sequences is involved in the alignment.

Other methods that may be used to align sequences are the alignment method of Needleman and Wunsch (Needleman and Wunsch. *J. Mol. Biol.,* 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48:1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations.

The term "analog" means an amino acid or nucleic acid sequence which has been modified as compared to the Slit sequences wherein the modification does not alter the utility of the sequence (e.g. binding to Robo) as described herein. The modified sequence or analog may have improved properties over the Slit sequences. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Slit protein may be modified to contain amino acid substitutions, insertions and/or deletions that do not alter the binding and/or activating properties of the protein. Conserved amino acid substitutions involve replacing one or more amino acids of the protein with amino acids of similar charge, size, and/or hydrophobicity characteristics. When only conserved substitutions are made the resulting analog should be functionally equivalent to Slit. Non-conserved substitutions involve replacing one or more amino acids of the conjugate protein with one or more amino acids which possess dissimilar charge, size, and/or hydrophobicity characteristics.

The disclosure further encompasses nucleic acid molecules that differ from any of the nucleic acid molecules disclosed herein in codon sequences due to the degeneracy of the genetic code.

Administration or use of a nucleic acid encoding Slit protein or variant thereof includes administration or use of a vector containing the nucleic acid molecule and the necessary regulatory sequences for the transcription and translation of the inserted sequence.

Suitable regulatory sequences may be derived from a variety of sources, including bacterial, fungal, viral, mammalian, or insect genes (for example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by Slit sequences and/or its flanking regions.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, Calif., U.S.A.).

In an embodiment, the methods and uses further comprise administration or use of another anti-fibrotic agent in combination with the Slit protein or nucleic acid. Other anti-fibrotic agents include, without limitation, ACE inhibitors and anti-TGF-β agents including, without limitation, antibodies.

The methods and uses described herein include administration or use of the Slit protein or nucleic acid alone or as part of a pharmaceutical composition comprising the Slit protein.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003-20$^{th}$ Edition) and in The United States Pharmacopeia: The National Formulary (USP 24 NF19) published in 1999).

On this basis, the pharmaceutical compositions for use in the methods and/or uses described herein include, albeit not exclusively, the active compound or substance in association with one or more pharmaceutically acceptable vehicles or diluents, and contained in buffered solutions with a suitable pH and iso-osmotic with the physiological fluids.

The pharmaceutical compositions may additionally contain other agents such as other anti-fibrotic agents. Accordingly, in another embodiment, the present disclosure provides a pharmaceutical composition comprising a Slit protein or nucleic acid and an additional anti-fibrotic agent. Other anti-fibrotic agents include, without limitation, ACE inhibitors and anti-TGF-β agents including, without limitation, antibodies.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

To study the effects of Slit2 on development of long-term fibrosis after acute kidney injury, a mouse model of unilateral kidney IRI was established (Furuichi et al., 2006; Feitoza et al., 2008; Ko et al., 2010). Clamping of one, rather than both, renal pedicle(s) permits prolonged survival of experimental mice and thus allows evaluation of late fibrosis and renal function (Furuichi et al., 2006; Feitoza et al., 2008; Ko et al., 2010). The left renal pedicle is cross-clamped for 45 min (Furuichi et al., 2006; Feitoza et al., 2008; Ko et al., 2010). Upon release of the clamp, the kidney is observed to ensure that reperfusion occurs. Sham surgery is similarly performed, without cross-clamping the renal vessels. A prolonged period of ischemia (ie 45 min) at the outset is needed to produce sufficient injury to cause late interstitial fibrosis (Furuichi et al., 2006; Feitoza et al., 2008; Ko et al., 2010). If both kidneys were subjected to this degree of ischemic injury, the mice would succumb early on to acute renal failure, and could not be used to study late events (Furuichi et al., 2006; Feitoza et al., 2008; Ko et al., 2010). In this model, early fibrotic changes are visible by 14 days and more robust fibrosis is evident at 28 days after induction of acute ischemia (Furuichi et al., 2006; Feitoza et al., 2008; Ko et al., 2010). In preliminary experiments, mice were subjected to renal artery clamping and release, or to sham surgery, of only the left kidney (Furuichi et al., 2006; Feitoza et al., 2008; Ko et al., 2010). A significant increase in renal fibrosis was seen even at 14 days.

Slit2 or control vehicle was injected intravenously 1 hour prior to inducing IRI and intraperitoneally (ip) every 3 d thereafter. To study the function of the injured kidney, the uninjured kidney was resected on Day 13. The injured kidney and blood were collected 1 d later, that is, 14 d after IRI (Furuichi et al., 2006; Feitoza et al., 2008; Ko et al., 2010).

Figure 6:
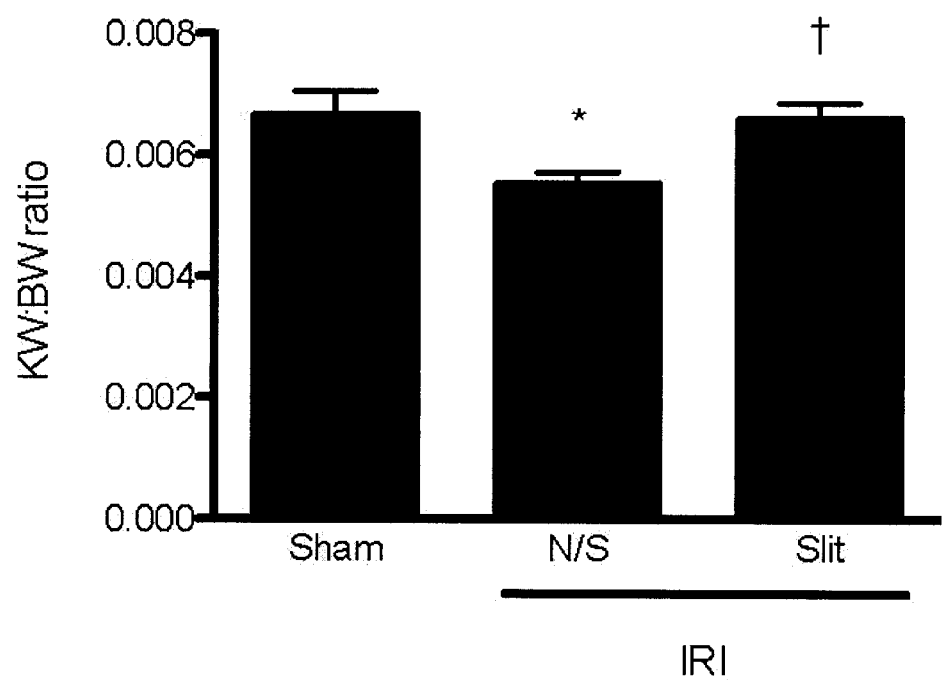
FIG. 6 shows Slit2 inhibits development of renal fibrosis after acute ischemic kidney injury. Male C57BL/6 mice underwent sham surgery or unilateral left-sided ischemia-reperfusion injury (IRI) as described in FIG. 1. IRI mice were treated either with normal saline or N-Slit2 as described in FIG. 1. Fourteen days after surgery, mice were sacrificed, and the left kidneys harvested. The ratio of the weight of the injured kidney: body weight (KW:BW) was determined for each mouse. As expected, even at this early time post-IRI the weights of the injured kidneys were less than those of sham-treated kidneys, likely reflecting more tubular drop-out and interstitial fibrosis in post-ischemic kidneys. Slit2 inhibited the decrease in kidney weight, restoring values back to those seen in sham-treated mice. Mean values±SEM from 4 mice per group.*$p<0.05$ vs. sham. † $p<0.05$ vs. N/S.

Mice underwent nephrectomy of the uninjured kidney 1 d prior to measurement of renal function, so that the plasma creatinine and urea reflect the function of the injured kidney, and not that of the uninjured kidney (Furuichi et al., 2006; Ko et al., 2010). Even at this early time, mice that received vehicle control had lower kidney weights than their sham-operated counterparts, reflecting loss of normal kidney tissue and development of more fibrosis (FIG. 6). Slit2 treatment resulted in significantly higher KW:BW, suggesting less fibrosis, even early after kidney IRI. At longer time points (28 d), this effect would be expected to be greatly pronounced. Plasma creatinine and urea concentration were measured using standard autoanalyzer methods (FIG. 1).

To assess fibrosis, the injured kidney was sectioned and stained with picrosirius red (PSR) to identify fibrillar collagen with red staining. (FIG. 2).

Figure 1:
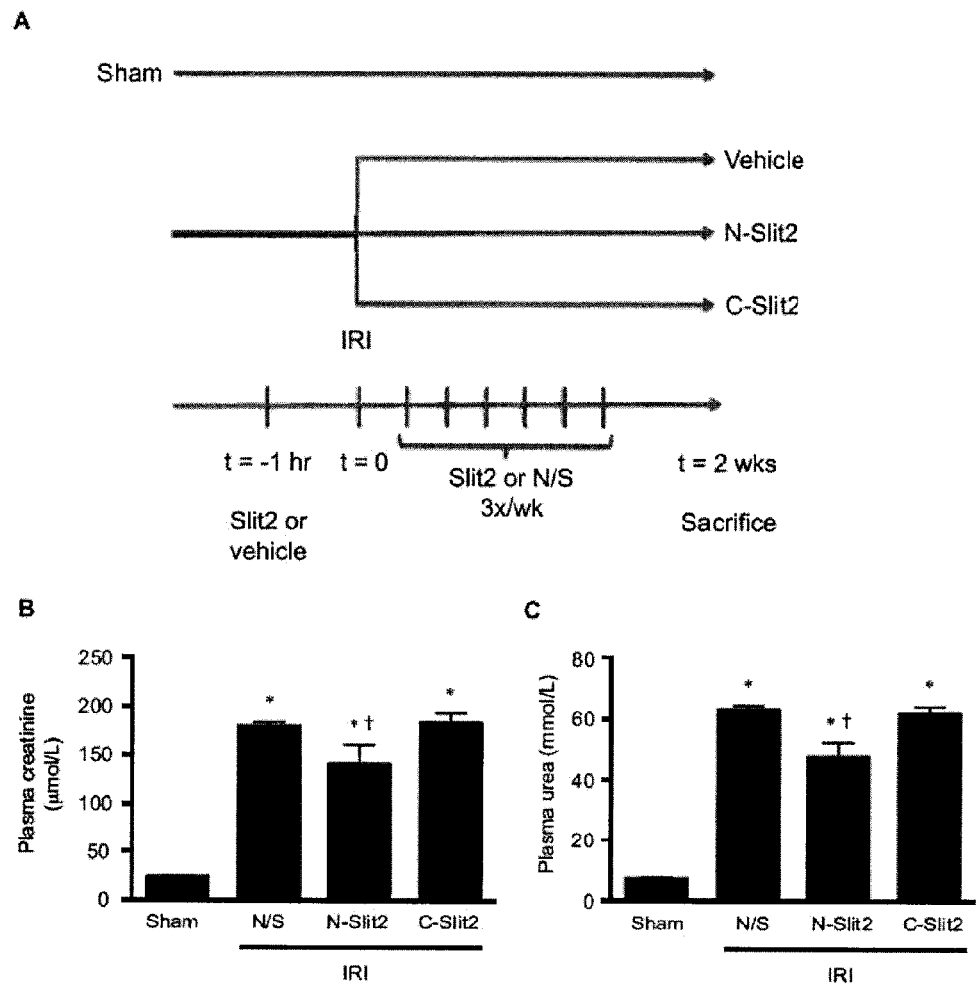
FIG. 1 shows treatment with N-Slit2 (active), but not C-Slit2 (inactive), prevents late ischemia-reperfusion IRI-associated renal dysfunction. (A) Male C57BL/6 mice underwent unilateral left kidney ischemia-reperfusion injury, characterized by renovascular pedicle clamping for 45 min under anesthesia, followed by clamp release and reperfusion. IRI mice were randomized to receive either 2 µg N-Slit2 (n=8), equimolar concentration 0.6 µg C-Slit2 (n=7), or normal saline (N/S) vehicle control (n=11). N-Slit2, C-Slit2, and N/S were administered via intravenous injection 1 h prior to IRI, followed by thrice weekly intraperitoneal injections in the 2 weeks following the surgery. A subset of mice underwent sham surgery during which kidneys were mobilized but uninjured to serve as healthy controls. Animals were followed for a total of 14 days, and then sacrificed for tissue and molecular analysis. One day prior to sacrifice, all animals underwent nephrectomy to remove the healthy right kidney. Blood was then collected prior to sacrifice, centrifuged, and plasma collected for measurement of renal function. (B) Plasma creatinine. (C) Plasma urea. *$p<0.05$ vs. sham operated controls. † $p<0.05$ vs. normal saline vehicle-treated IRI animal.
Figure 2:
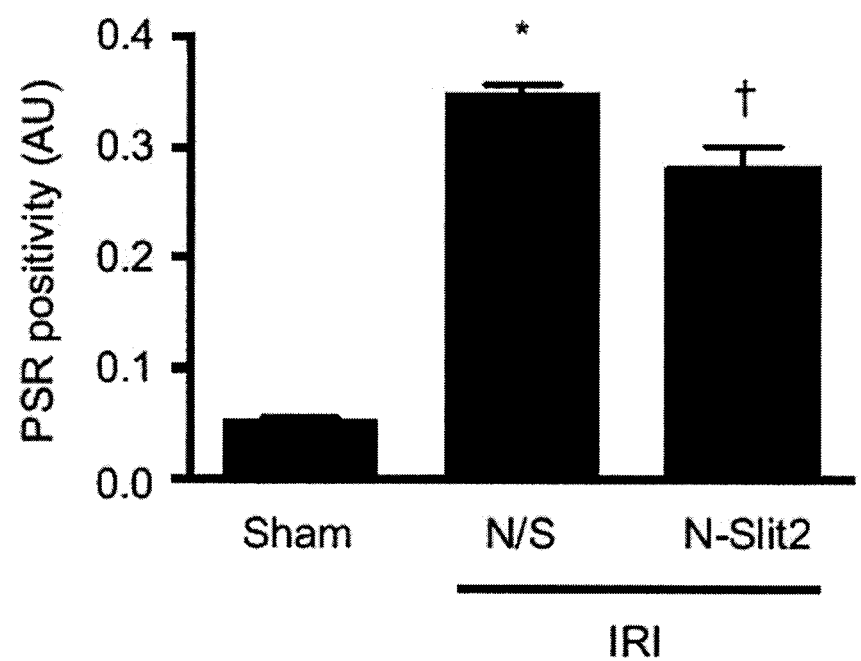
FIG. 2 shows N-Slit2 administration attenuates kidney fibrosis induced by ischemia-reperfusion injury (IRI). Male C57BL/6 mice underwent sham surgery or unilateral left-sided ischemia-reperfusion injury (IRI) as described in FIG. 1. IRI mice were treated either with normal saline or N-Slit2 as described in FIG. 1. Fourteen days after surgery, mice were sacrificed, and the left kidneys harvested, sectioned, and stained with picrosirius red (PSR) to identify fibrillar collagen with red staining. Whole-section digital analysis of PSR-stained kidneys demonstrated a significant increase in fibrillar collagen deposition in normal saline (N/S)-treated IRI mice compared with sham mice. N-Slit2 treatment partially attenuated this fibrotic response. 20× images were obtained for sham control kidneys, N/S-treated IRI kidney, and N-Slit2-treated IRI kidney and from the images, quantitative analysis of PSR staining is shown. *$p<0.05$ vs. sham operated controls. † $p<0.05$ vs. N/S vehicle-treated IRI mice. Abbreviations: AU, arbitrary units.

Mice that received Slit2 had preserved kidney weight, less renal fibrosis and better renal function than mice treated with vehicle control (FIGS. 1, 2, and 6). These studies suggest that administration of Slit2 can prevent long-term renal fibrosis after AKI.

Figure 3:
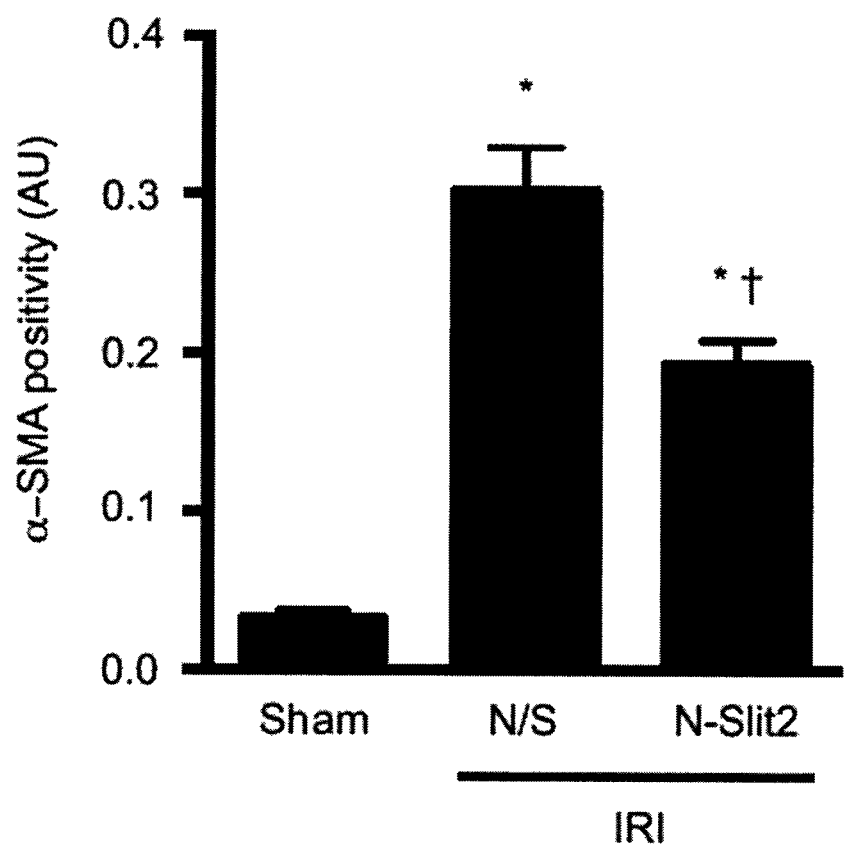
FIG. 3 shows N-Slit2 treatment attenuates renal fibroblast activation post-ischemia-reperfusion injury. Male C57BL/6 mice underwent sham surgery or left-sided renal ischemia-reperfusion injury as described in FIG. 1. IRI mice were treated either with normal saline or N-Slit2, and kidneys harvested and prepared as described in FIG. 1. Kidney sections were then immunostained with an anti-α-smooth muscle actin (α-SMA) antibody followed by a horseradish peroxidase-conjugated secondary antibody. Whole-section digital analysis of α-SMA-stained kidneys demonstrated a significant increase in fibroblast activation in normal saline (N/S)-treated IRI mice compared with sham mice. N-Slit2 treatment partially attenuated IRI-associated fibroblast activation. *$p<0.05$ vs. sham operated controls. † $p<0.05$ vs. N/S vehicle-treated IRI mice. Abbreviations: AU, arbitrary units.

To determine whether Slit2-treated mice exhibit less myofibroblast infiltration in the renal interstitium, immunostaining was done using Ab that detects α-smooth muscle actin (α-SMA), a mesenchymal marker abundantly expressed by myofibroblasts (FIG. 3). The amount of renal cortex and medulla occupied by α-SMA was determined (FIG. 3) (Furuichi et al., 2006; Feitoza et al., 2008).

Figure 4:
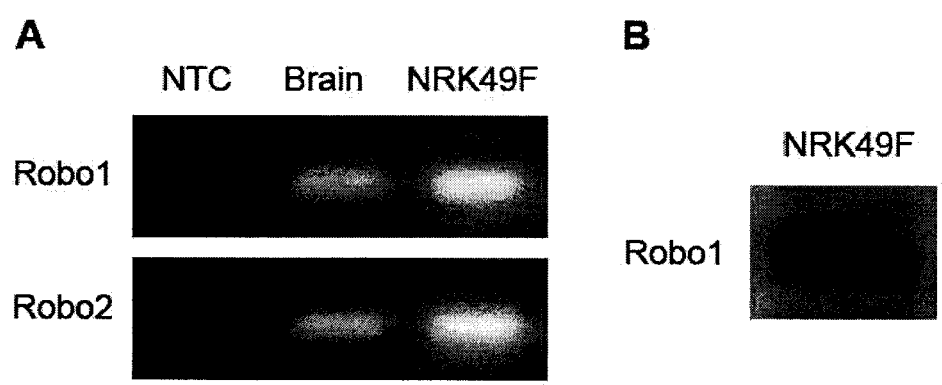
FIG. 4 shows (A) renal fibroblast cells express Robo-1 and Robo-2 receptors for Slit proteins. RNA was isolated from cultured NRK49F rat renal fibroblasts, and rat brain tissue. Forty cycles of one-step reverse transcription PCR were performed. Robo-1 and Robo-2 mRNA was detected in rat brain (positive control), and also in cultured rat renal fibroblasts. (B) Immunoblotting was performed using an antibody detecting Robo-1 and lysates isolated from NRK-49F cells. Robo-1 protein was detected in these cells. NTC refers to a no template control.

To determine whether Slit2 could directly act on fibroblasts, RT-PCR was performed on RNA isolated from NRK-49F renal fibroblasts and it was confirmed that these cells express both Robo-1 and Robo-2 (FIG. 4). Robo-1 expression in cultured NRK49F rat renal fibroblasts was also detected by immunoblotting (FIG. 4) and immunostaining with an anti-Robo-1 antibody.

Figure 5:
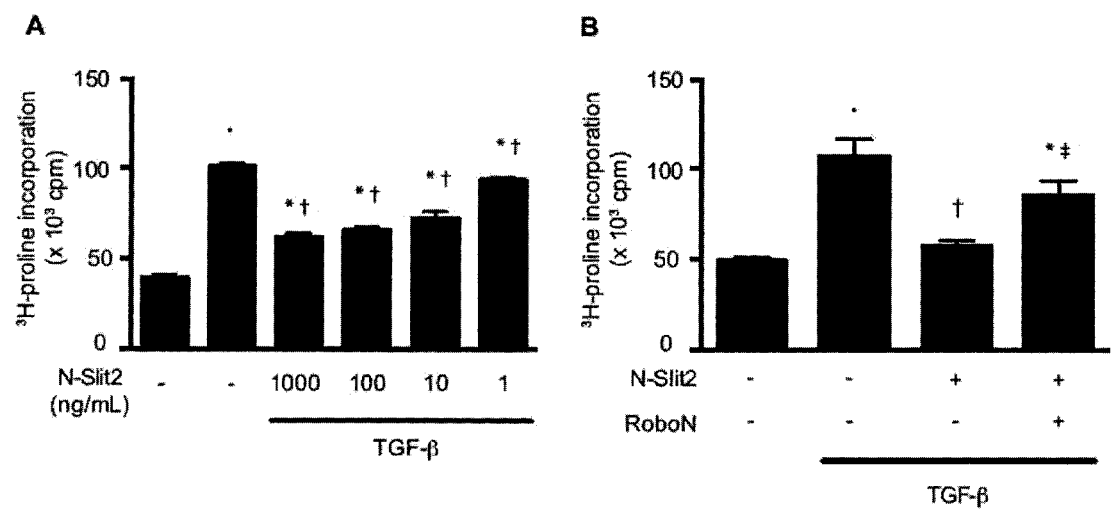
FIG. 5 shows N-Slit2 inhibits TGF-β-induced renal fibroblast collagen production. Cultured NRK49F rat renal fibroblasts were serum starved in DMEM containing 0.5% bovine serum albumin (BSA) overnight, followed by incubation with [$^3$H]-proline and stimulation with TGF-β 4 ng/mL. Forty four hours later, protein was acid precipitated and unincorporated [$^3$H]-proline washed off. As collagen is highly enriched in proline amino acid residues, the scintillation count ([$^3$H]-proline incorporation) from precipitated protein is directly proportional to the amount of collagen produced. (A) Thirty minute pre-treatment of NRK49F cells with N-Slit2 induced a dose-dependent reduction in TGF-β-induced collagen production. (B) In parallel experiments, NRK49F cells were pre-treated with either N-Slit2 250 ng/mL or N-Slit2 250 ng/mL mixed with molar equivalent amounts of RoboN, a soluble decoy receptor for N-Slit2. Mixing of N-Slit2 with its soluble decoy receptor blocked its inhibitory effect on TGF-β-induced fibroblast collagen production. *$p<0.05$ vs. unstimulated fibroblasts. † $p<0.05$ vs. TGF-β-stimulated fibroblasts. ‡ $p<0.05$ vs. N-Slit2- and TGF-β-treated fibroblasts. Abbreviations: cpm, counts per minute.

Slit2 specifically decreased $^3$H-proline incorporation in TGF-β-treated NRK49F rat renal fibroblasts, suggesting a decrease in collagen synthesis (FIG. 5) (Furuichi et al., 2006; Yuen et al., 2010). These results indicate that Slit2 may directly act on renal fibroblasts to inhibit their secretion of collagenous matrix, a key element of the progressive fibrosis that follows AKI.

Example 2

Slit2 Regulates Glomerular Angiogenesis and Hyperfiltration in Diabetes

Figure 7:
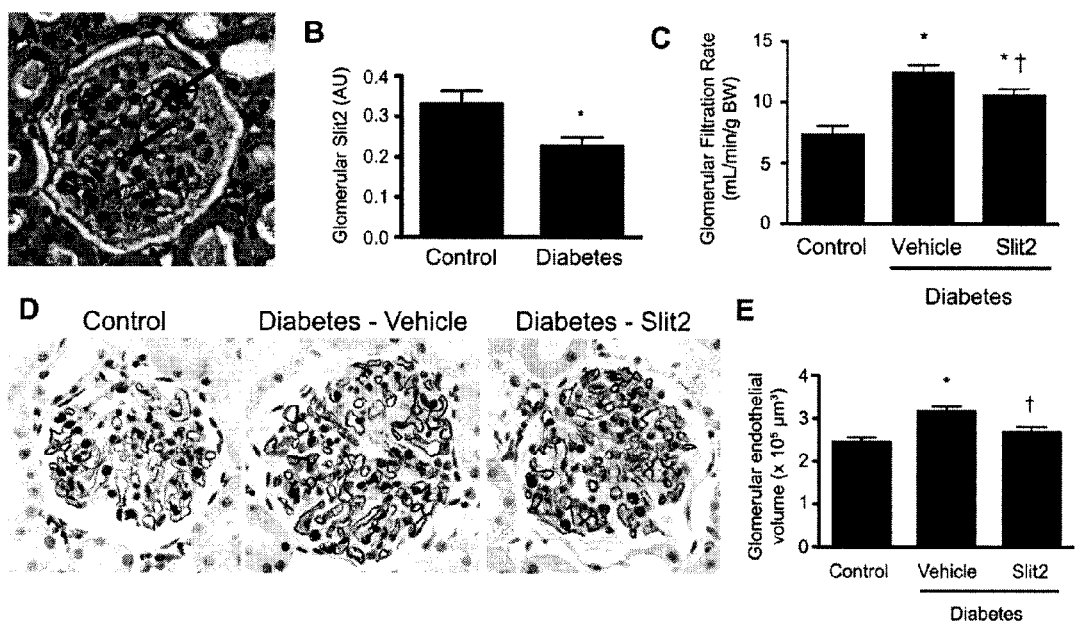
FIG. 7 shows (A) Slit2 localizes primarily to endothelial cells (arrows) in healthy rat glomerulus. After 3 wks of STZ-induced diabetes, rats demonstrate (B) reduced glomerular Slit2 protein, (C) hyperfiltration, and (D-E) increased glomerular endothelial volume. Thrice weekly i.p. injections of 2 µg of Slit2 attenuated increases in (C) GFR and (D-E)

Building upon data describing Slit2-Robo4 signaling as an anti-angiogenic regulatory pathway [Jones et al. 2008; Jones et al. 2009; Marlow et al. 2010], it was recently discovered that glomerular endothelium expresses both Slit2 and Robo4, and that glomerular Slit2 is downregulated following the onset of experimental diabetes, a change that coincides with glomerular neovascularization and hyperfiltration (FIG. 7). Illustrating the importance of Slit2 as an inhibitor of pathologic diabetic endothelial injury, i.p. injections of Slit2 abrogated streptozotocin (STZ)-induced glomerular capillary growth and hyperfiltration (FIG. 7). Given the link between hyperfiltration and poor long-term kidney outcomes, the data suggests the potential for Slit2 as a therapy to arrest progression of early diabetic nephropathy by targeting diabetes-induced neovascularization.

Example 3

Slit2 is a Potent Anti-fibrotic TGF-b-inhibitory Agent in NRK49F Rat Renal Fibroblasts As fibroblast activation is dependent on actin rearrangements [Hubchak et al. 2003], whether Slit2 might regulate renal fibrogenesis was also examined. It was first demonstrated that both mesangial cells and renal fibroblasts express the Slit2 receptor Robo1. Next, it was found that Slit2 inhibits TGF-β-induced fibroblast RhoA activation and Smad2 phosphorylation, two key pro-fibrotic pathways activated by TGF-β (FIG. 8). Not surprisingly, Slit2 inhibited TGF-β-induced fibroblast collagen production (FIG. 8).

Example 4

Slit2 Inhibits Renal Fibrosis in Two Independent Mouse Models of Chronic Kidney Disease Slit2 administration blocked renal fibrogenesis in two independent mouse models of kidney fibrosis, leading to improvements in renal function (FIG. 9). This new and previously undescribed anti-fibrotic activity suggests that in addition to targeting the glomerular neovascularization that characterizes early disease, Slit2 may also be useful for the prevention of fibrosis in more advanced diabetic nephropathy.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES (1993) The effect of intensive treatment of diabetes on the development and progression of long-term complications in insulin-dependent diabetes mellitus. The Diabetes Control and Complications Trial Research Group. N Engl J Med 329: 977-986.

(1998) Intensive blood-glucose control with sulphonylureas or insulin compared with conventional treatment and risk of complications in patients with type 2 diabetes (UKPDS 33). UK Prospective Diabetes Study (UKPDS) Group. Lancet 352: 837-853.

Adler A I, Stratton I M, Neil H A, Yudkin J S, Matthews D R, et al. (2000) Association of systolic blood pressure with macrovascular and microvascular complications of type 2 diabetes (UKPDS 36): prospective observational study. BMJ 321: 412-419.

Amdur, R. L., Chawla, L. S., Amodeo, S., Kimmel, P. L., and Palant, C. E. 2009. Outcomes following diagnosis of acute renal failure in U.S. veterans: focus on acute tubular necrosis. Kidney Int 76:1089-1097.

Anderson S, Rennke H G, Brenner B M (1986) Therapeutic advantage of converting enzyme inhibitors in arresting progressive renal disease asociated with systemic hypertension in the rat. J Clin Invest 77: 1993-2000.

Anderson S, Jung F F, Ingelfinger J R (1993) Renal renin-angiotensin system in diabetes: functional, immunohistochemical, and molecular biological correlations. Am J Physiol 265: F477-486.

Battye, R., Stevens, A., Perry, R., and Jacobs, J. 2001. Repellent activity by Slit requires the leucine-rich repeats. J Neurosci 21:4290-4298.

Bhowmick N A, Ghiassi M, Bakin A, Aakre M, Lundquist C A, et al. (2001) Transforming growth factor-beta1 mediates epithelial to mesenchymal transdifferentiation through a RhoA-dependent mechanism. Mol Biol Cell 12: 27-36

Bonventre, J. V., and Yang, L. 2011. Cellular pathophysiology of ischemic acute kidney injury. J Clin Invest 121: 4210-4221.

Brenner B M, Cooper M E, de Zeeuw D, Keane W F, Mitch W E, et al. (2001) Effects of losartan on renal and cardiovascular outcomes in patients with type 2 diabetes and nephropathy. N Engl J Med 345: 861-869.

Brose, K., Bland, K. S., Wang, K. H., Arnott, D., Henzel, W., Goodman, C. S., Tessier-Lavigne, M., and Kidd, T. 1999. Slit proteins bind Robo receptors and have an evolutionarily conserved role in repulsive axon guidance. Cell 96:795-806.

Chawla, L. S., and Kimmel, P. L. 2012. Acute kidney injury and chronic kidney disease: an integrated clinical syndrome. Kidney Int 82:516-524.

Chawla, L. S., Amdur, R. L., Amodeo, S., Kimmel, P. L., and Palant, C. E. 2011. The severity of acute kidney injury predicts progression to chronic kidney disease. Kidney Int 79:1361-1369.

Chen, J., Wen, L., Dupuis, S., Wu, J., and Rao, Y. 2001. The N-terminal leucine rich regions in Slit are sufficiently to repel olfactory bulb axons and subventricular zone neurons. J Neurosci 21:1548-1556.

Costacou T, Ferrell R E, Ellis D, Orchard T J (2009) Haptoglobin genotype and renal function decline in type 1 diabetes. Diabetes 58: 2904-2909

Engel M E, McDonnell M A, Law B K, Moses H L (1999) Interdependent SMAD and JNK signaling in transforming growth factor-beta-mediated transcription. J Biol Chem 274: 37413-37420

Feitoza, C. Q., Goncalves, G. M., Semedo, P., Cenedeze, M. A., Pinheiro, H. S., Beraldo, F. C., dos Santos, O. F., Teixeira Vde, P., dos Reis, M. A., Mazzali, M., et al. 2008. Inhibition of COX 1 and 2 prior to renal ischemia/reperfusion injury decreases the development of fibrosis. Mol Med 14:724-730.

Furuichi, K., Gao, J.-L., and Murphy, P. M. 2006. Chemokine receptor CX3CR1 regulates renal interstitial fibrosis after ischemia-reperfusion injury. Am J Pathol 169:372-387.

Gilbert R E, Cooper M E (1999) The tubulointerstitium in progressive diabetic kidney disease: more than an aftermath of glomerular injury? Kidney Int 56: 1627-1637

Gordois A, Scuffham P, Shearer A, Oglesby A (2004) The health care costs of diabetic nephropathy in the United States and the United Kingdom. J Diabetes Complications 18: 18-26.

Grieshammer, U., Ma, L., Plump, A., and Martin, G. 2004. SLIT2-mediated ROBO2 signaling restricts kidney induction to a single site. Dev Cell 6:709-717.

Hirose K, Tsuchida H, Osterby R, Gundersen H J (1980) A strong correlation between glomerular filtration rate and filtration surface in diabetic kidney hyperfunction. Lab Invest 43: 434-437.

Hubchak S C, Runyan C E, Kreisberg J I, Schnaper H W (2003) Cytoskeletal rearrangement and signal transduction in TGF-beta1-stimulated mesangial cell collagen accumulation. J Am Soc Nephrol 14: 1969-1980

Jones C A, London N R, Chen H, Park K W, Sauvaget D, et al. (2008) Robo4 stabilizes the vascular network by inhibiting pathologic angiogenesis and endothelial hyperpermeability. Nat Med 14: 448-453

Jones C A, Nishiya N, London N R, Zhu W, Sorensen L K, et al. (2009) Slit2-Robo4 signalling promotes vascular stability by blocking Arf6 activity. Nat Cell Biol 11: 1325-1331

Kanellis, J., Garcia, G. E., Li, P., Parra, G., Wilson, C. B., Han, S., Smith, C. W., Johnson, R. J., Wu, J. Y., and Feng, L. 2004. Modulation of inflammation by Slit protein in vivo in experimental crescentic glomerulonephritis. Am J Pathol 165:341-351.

Kida, Y., and Duffield, J. S. 2011. Pivotal role of pericytes in kidney fibrosis. Clin Exp Pharmacol Physiol 38:467-473.

Kidd, T., Bland, K., and Goodman, C. 1999. Slit is the midline repellent for the Robo receptor in Drosophila. Cell 96:785-794.

Ko, G. J., Grigoryev, D. N., Linfert, D., Jang, H. R., Watkins, T., Cheadle, C., Racusen, L., and Rabb, H. 2010. Transcriptional analysis of kidneys during repair from AKI reveals possible roles for NGAL and KIM-1 as biomarkers of AKI-to-CKD transition. Am J Physiol Renal Physiol 298:F1472-1483.

Lewis E J, Hunsicker L G, Bain R P, Rohde R D (1993) The effect of angiotensin-converting-enzyme inhibition on diabetic nephropathy. The Collaborative Study Group. N Engl J Med 329: 1456-1462.

Lewis E J, Hunsicker L G, Clarke W R, Berl T, Pohl M A, et al. (2001) Renoprotective effect of the angiotensin-receptor antagonist irbesartan in patients with nephropathy due to type 2 diabetes. N Engl J Med 345: 851-860.

Lin, S. L., Chang, F. C., Schrimpf, C., Chen, Y. T., Wu, C. F., Wu, V. C., Chiang, W. C., Kuhnert, F., Kuo, C. J., Chen, Y. M., et al. 2011. Targeting endothelium-pericyte cross talk by inhibiting VEGF receptor signaling attenuates kidney microvascular rarefaction and fibrosis. Am J Pathol 178:911-923.

Liu, D., Hou, J., Hu, X., Wang, X., Xiao, Y., Mou, Y., and De Leon, H. 2006. Neuronal chemorepellent Slit2 inhibits vascular smooth muscle cell migration by suppressing small GTPase Rac1 activation. Circ Res 98:480-489.

Lo, L. J., Go, A. S., Chertow, G. M., McCulloch, C. E., Fan, D., Ordonez, J. D., and Hsu, C. Y. 2009. Dialysis-requiring acute renal failure increases the risk of progressive chronic kidney disease. Kidney Int 76:893-899.

Magee G M, Bilous R W, Cardwell C R, Hunter S J, Kee F, et al. (2009) Is hyperfiltration associated with the future risk of developing diabetic nephropathy? A meta-analysis. Diabetologia 52: 691-697.

Marlow R, Binnewies M, Sorensen L K, Monica S D, Strickland P, et al. (2010) Vascular Robo4 restricts proangiogenic VEGF signaling in breast. Proc Natl Acad Sci U S A 107: 10520-10525

Nguyen Ba-Charvet, K. T., Brose, K., Ma, L., Wang, K. H., Marillat, V., Sotelo, C., Tessier-Lavigne, M., and Chedotal, A. 2001. Diversity and specificity of actions of Slit2 proteolytic fragments in axon guidance. J Neurosci 21:4281-4289.

Patel, S., Huang, Y. W., Reheman, A., Pluthero, F. G., Chaturvedi, S., Mukovozov, I. M., Tole, S., Liu, G. Y., Li, L., Durocher, Y., Ni, H., Kahr, W. H. A., and Robinson, L. A. 2012. The cell motility modulator Slit2 is a potent inhibitor of platelet function. Circulation 126:1385-1395.

Piper, M., Georgas, K., Yamada, T., and Little, M. 2000. Expression of the vertebrate Slit gene family and their putative receptors, the Robo genes, in the developing kidney. Mech Dev 94:213-217.

Prasad, A., Qamri, Z., Wu, J., and Ganju, R. K. 2007. Slit-2/Robo-1 modulates the CXCL12/CXCR4-induced chemotaxis of T cells. J Leukoc Biol 82:465-476.

Prasad, A., Fernandis, A. Z., Rao, Y., and Ganju, R. K. 2004. Slit protein-mediated inhibition of CXCR4-induced chemotactic and chemoinvasive signaling pathways in breast cancer cells. J Biol Chem 279:9115-9124.

Quaggin, S. E., and Kapus, A. 2011. Scar wars: mapping the fate of epithelial-mesenchymalmyofibroblast transition. Kidney Int 80:41-50.

Ronca, F., Andersen, J. S., Paech, V., and Margolis, R. U. 2001. Characterization of Slit protein interactions with glypican-1. J Biol Chem 276:29141-29147.

Rossing P (2006) Diabetic nephropathy: worldwide epidemic and effects of current treatment on natural history. Curr Diab Rep 6: 479-483.

Ruggenenti P, Porrini E L, Gaspari F, Motterlini N, Cannata A, et al. (2012) Glomerular hyperfiltration and renal disease progression in type 2 diabetes. Diabetes Care 35: 2061-2068.

Schimmelpfeng, K., Gogel, S., and Klambt, C. 2001. The function of leak and kuzbanian during growth cone and cell migration. Mech Dev 106:25-36.

Schrimpf, C., and Duffield, J. S. 2011. Mechanisms of fibrosis: the role of the pericyte. Curr Opin Nephrol Hypertens 20:297-305.

Sochett E B, Cherney D Z, Curtis J R, Dekker M G, Scholey J W, et al. (2006) Impact of renin angiotensin system modulation on the hyperfiltration state in type 1 diabetes. J Am Soc Nephrol 17: 1703-1709

Tole, S., Mukovozov, I. M., Huang, Y. W., Magalhaes, M. A., Yan, M., Crow, M. R., Liu, G. Y., Sun, C. X., Durocher, Y., Glogauer, M., and Robinson, L. A. 2009. The axonal repellent, Slit2, inhibits directional migration of circulating neutrophils. J Leukoc Biol 86:1403-1415.

Venkatachalam, M. A., Griffin, K. A., Lan, R., Geng, H., Saikumar, P., and Bidani, A. K. 2010. Acute kidney injury: a springboard for progression in chronic kidney disease. Am J Physiol Renal Physiol.

Wald, R., Quinn, R. R., Adhikari, N. K., Burns, K. E., Friedrich, J. O., Garg, A. X., Harel, Z., Hladunewich, M. A., Luo, J., Mamdani, M., et al. 2012. Risk of chronic dialysis and death following acute kidney injury. Am J Med 125:585-593.

Wald, R., Quinn, R. R., Luo, J., Li, P., Scales, D. C., Mamdani, M. M., and Ray, J. G. 2009. Chronic dialysis and death among survivors of acute kidney injury requiring dialysis. JAMA 302:1179-1185.

Wang, K., Brose, K., Arnott, D., Kidd, T., Goodman, C., Henzel, W., and Tessier-Lavigne, M. 1999. Biochemical purification of a mammalian slit protein as a positive regulator of sensory axon elongation and branching. Cell 96:771-784.

Wong, K., Ren, X.-R., Huang, Y.-Z., Xie, Y., Liu, G., Saito, H., Tang, H., Wen, L., Brady-Kalnay, S. M., Mei, L., et al. 2001. Signal transduction in neuronal migration: roles of GTPase activating proteins and the small GTPase Cdc42 in the Slit-Robo pathway. Cell 107:209-221.

Wu, J. Y., Feng, L., Park, H.-T., Havlioglu, N., Wen, L., Tang, H., Bacon, K. B., Jiang, Z.-h., Zhang, X.-c., and Rao, Y. 2001. The neuronal repellent Slit inhibits leukocyte chemotaxis induced by chemotactic factors. Nature 410:948-952.

Yip J W, Jones S L, Wiseman M J, Hill C, Viberti G (1996) Glomerular hyperfiltration in the prediction of nephropathy in IDDM: a 10-year follow-up study. Diabetes 45: 1729-1733.

Yu, J., McMahon, A., and Valerius, M. T. 2004. Recent genetic studies of mouse kidney development. Curr Opin Genet Dev 14:550-557.

Yuen, D. A., Connelly, K. A., Advani, A., Liao, C., Kuliszewski, M. A., Trogadis, J., Thai, K., Advani, S. L., Zhang, Y., Kelly, D. J., et al. 2010. Culture-modified bone marrow cells attenuate cardiac and renal injury in a chronic kidney disease rat model via a novel antifibrotic mechanism. PLoS One 5:e9543.

Zeisberg, M., and Neilson, E. G. 2010. Mechanisms of tubulointerstitial fibrosis. J Am Soc Nephrol 21:1819-1834.

The invention claimed is:

1. A method of inhibiting fibrosis comprising administering a Slit protein or a functional variant thereof or nucleic acid encoding a Slit protein or a functional variant thereof to an animal in need thereof; wherein the animal has chronic kidney disease and wherein the functional variant has at least 90% identity to the Slit protein.

2. The method of claim 1, wherein the fibrosis is due to increased collagen deposition and/or synthesis.

3. A method of treating fibrosis in an animal that has chronic kidney disease comprising administering a Slit protein or a functional variant thereof or nucleic acid encoding a Slit protein or a functional variant thereof to the animal in need thereof; wherein the functional variant has at least 90% identity to the Slit protein.

4. The method of claim 3, wherein the Slit2 protein or nucleic acid is administered 5 days after an acute kidney injury, or later.

5. The method of claim 4, wherein the Slit2 protein or nucleic acid is administered 10 days after an acute kidney injury, or later.

6. The method of claim 3, wherein the subject with chronic kidney disease has a glomerular filtration rate of less than 60 ml/min/1.73 m$^2$.

7. The method of claim 3, wherein the subject with chronic kidney disease is at stage 3 or greater.

8. The method of claim 1, wherein the Slit protein or nucleic acid is suitable for daily, weekly or monthly use.

9. The method of claim 1, wherein the Slit protein or nucleic acid is suitable for local administration.

10. The method of claim 1, wherein the Slit protein or nucleic acid is suitable for long-term use.

11. The method of claim 1, wherein the Slit protein or functional variant thereof is Slit1, 2 or 3.

12. The method of claim 11, wherein the Slit protein or functional variant thereof is Slit2 or Slit2-N.

13. The method of claim 3, wherein the Slit protein or nucleic acid is suitable for daily, weekly or monthly use.

14. The method of claim 3, wherein the Slit protein or nucleic acid is suitable for local administration.

15. The method of claim 3, wherein the Slit protein or nucleic acid is suitable for long-term use.

16. The method of claim 3, wherein the Slit protein or functional variant thereof is Slit1, 2 or 3.

17. The method of claim 16, wherein the Slit protein or functional variant thereof is Slit2 or Slit2-N.

\* \* \* \* \*